(12) United States Patent
Bilyeu

(10) Patent No.: US 7,196,249 B1
(45) Date of Patent: Mar. 27, 2007

(54) SOYBEAN VARIETY S04-97130-15-02

(75) Inventor: Keith Bilyeu, Ames, IA (US)

(73) Assignee: Garst Seed Company, Slater, IA (US)

( * ) Notice: Subject to any disclaimer, the term of this patent is extended or adjusted under 35 U.S.C. 154(b) by 338 days.

(21) Appl. No.: 10/789,917

(22) Filed: Feb. 27, 2004

(51) Int. Cl.
*A01H 5/00* (2006.01)
*A01H 5/10* (2006.01)
*A01H 1/00* (2006.01)
*A01H 1/02* (2006.01)

(52) U.S. Cl. .................. 800/312; 800/260; 800/279; 800/300; 800/302; 800/303; 435/415; 435/426; 435/430; 435/430.1

(58) Field of Classification Search ............... 800/312, 800/260, 279, 300, 302, 303; 435/415, 426, 435/430, 430.1
See application file for complete search history.

(56) References Cited

U.S. PATENT DOCUMENTS 6,369,300 B1 * 4/2002 Freestone et al. ........... 800/312

* cited by examiner

*Primary Examiner*—Cynthia Collins
(74) *Attorney, Agent, or Firm*—Dana S. Rewoldt

(57) ABSTRACT

The present invention is in the field of soybean variety S04-97130-15-02 breeding and development. The present invention particularly relates to the soybean variety S04-97130-15-02 and its progeny, and methods of making S04-97130-15-02.

13 Claims, No Drawings

SOYBEAN VARIETY S04-97130-15-02

THE FIELD OF THE INVENTION

The present invention is in the field of soybean variety S04-97130-15-02 breeding and development. The present invention particularly relates to the soybean variety S04-97130-15-02 and its progeny, and methods of making.

BACKGROUND OF THE INVENTION

Soybean Glycine max (L) is an important oil seed crop and a valuable field crop. The breeding and development of crops has been ongoing across the last 1000 years. The pace of this development in soybeans, as an animal foodstuff and as an oil seed has dramatically increased in the last one hundred years. Planned programs of soybean breeding have increased the growth, yield and environmental hardiness of the soybean germplasm.

Due to the sexual reproduction traits of the soybean, the plant is basically self-pollinating. A self-pollinating plant permits pollen from one flower to be transferred to the same or another flower of the same plant. Cross-pollination occurs when the flower is pollinated with pollen from a different plant; however, soybean cross pollination is a rare occurrence in nature.

Thus the growth and development of new soybean germplasm requires intervention by the breeder in the pollination of the soybean. The breeders' methods of intervening in the pollination depend on the type of trait that is being bred. Soybeans are developed for a number of different types of traits morphological (form and structure), phenotypical, for growth habit, daylength, temperature requirements, initiation date of floral or reproductive development and yield. The genetic complexity of the trait drives the breeding method.

Due to the number of genes within each chromosome, millions of genetic combinations exist in the breeders' experimental soybean material. This genetic diversity is so vast that a breeder cannot produce the same two cultivars twice using the exact same material. Thus, developing a single variety of useful commercial soybean germplasm is highly unpredictable, and requires intensive research.

The development of new soybeans comes through breeding techniques, such as: recurrent selection, mass selections, backcrossing, single seed descent and multiple seed procedure, which is used to save labor costs. Other breeding methods are know and are described in various soybean textbooks.

When the variety is being employed to develop a new variety or an improved variety the selection methods include backcrossing, pedigree breeding, recurrent selection, modified selection and mass selection. The efficiency of the breeding procedure is the driver that determines which of the selection techniques are employed. The determination of the efficiency of any breeding procedure requires a continuous evaluation of the success of the breeding program. The success is usually measured by yield increase, commercial appeal and environmental adaptability of the developed germplasm.

The development of soybean cultivars most often requires the development of hybrid crosses (some exceptions being initial development of mutants directly through the use of the mutating agent, trait introgression by markers, or transformants made directly through transformation methods) and the selection of progeny therefrom. Hybrids can be achieved by manual manipulation of the sexual organs of the soybean or by the use of male sterility systems. The breeder attempts to identify true hybrids by a readily identifiable trait. These hybrids are then selected and repeatedly selfed and reselected to form new homozygous lines from the heterozygous hybrids.

Outcrossing to a number of different parents creates breeding populations of fairly heterozygous populations. These populations are produced and used in pedigree breeding and recurrent selection. Pedigree breeding is commonly used with two parents which possess favorable, complementary traits. The parents are crossed to form a F1 hybrid. The progeny of the F1 hybrid is selected and the best individual F2s are selected; this selection process is repeated in the F3 and F4 generations. The inbreeding is carried forward and at F5–F7 the best lines are selected and tested in the development stage for potential usefulness in a selected geographic area.

Mass and recurrent selection can be used to improve populations. Several parents are intercrossed and plants are selected based on selected characteristics like superiority or excellent progeny.

In backcross breeding a genetic allele or loci is transferred into a desirable homozygous recurrent parent. The trait is in the donor parent and is tracked into the recurrent parent. The resultant plant is like the recurrent parent with the new desired allele or loci.

The single-seed descent method involves use of a segregating plant population for harvest of one seed per plant. Each seed sample is planted and the next generation is formed. When the F2 lines are advanced to F6 each plant will be derived from a different F2. The population will decline due to failure of some seeds, so not all F2 plants will be represented in the progeny.

New varieties must be tested thoroughly to compare their development with commercially available soybeans. This testing usually requires at least two years and up to six years of comparisons with other commercial soybeans. Varieties that lack the entire desirable package of traits can be used as parents in new populations for further selection or more often is simply discarded. The breeding and associated testing process is 8 to 12 years' of work prior to development of a new variety. Thousands of varietal lines are produced but only a few lines are selected in each step of the process. Thus the breeding system is like a funnel with numerous lines and selections in the first few years and fewer and fewer lines in the middle years until one line is selected for the final development testing.

The selected line or variety will be evaluated for its growth, development and yield. These traits of a soybean are a result of the variety's genetic potential interacting with its environment. All varieties have a maximum yield potential that is predetermined by its genetics. This hypothetical potential for yield is only obtained when the environmental conditions are perfect. Since prefect growth conditions do not exist, field experimentation is necessary to provide the environmental influence and to measure its effect on the development and yield of the soybean. The breeder attempts to select for good soybean yield potential under a number of different environmental conditions.

Selecting for good soybean yield potential in different environmental conditions is a process that requires planning based on the analysis of data in a number of seasons. Identification of the varieties carrying a superior combination of traits which will give consistent yield potential is a complex science. The desireable genotypic traits in the variety can often be masked by other plant traits, unusual weather patterns, diseases, and insect damage. One widely employed method of identifying a superior plant with such genotypic traits is to observe its performance relative to commercial and experimental plants in replicated studies. These types of studies give more certainty to the genetic potential and value of the plant.

In summary, the goal of the soybean plant breeder is to produce new and unique soybeans and progeny of the soybeans for farmers commercial crop production. To accomplish this the plant breeder painstakingly crosses two or more varieties or germplasm. Then the results of this cross is repeatedly selfed or backcrossed to produce new genetic patterns. Newer avenues for producing new and unique genetic alleles into soybeans include introducing mutations or transgenes into the genetic material of the soybean are now in practice in the breeding industry. These genetic alleles can alter herbicide resistance, fatty acid compositions, and amino acid compositions of the soybean plant or its seed.

The traits a breeder selects for when developing new soybeans is driven by the ultimate goal of the end user of the product. Thus if the goal of the end user is to resist a certain plant disease so overall more yield is achieved, then the breeder drives the introduction of genetic alleles and their selection based on disease resistant levels shown by the plant. On the other hand, if the goal is to produce a specific oil, with a high level of oleic acid and a lower level of linoleic acid, then the breeder may drive the selection of genetic alleles based on levels of fatty acids in the seed and accept some lesser yield potentials or other less desirable agronomic traits.

The new genetic alleles being introduced in to soybeans are widening the potential uses and markets for the various products and by-products of the oil from the seed plants such as soybean. A major product extracted from soybeans is the oil in the seed. Soybean oil is employed in a number of retail products such as cooking oil, baked goods, margarines and the like. Another useful product is soybean meal, which is a component of many foods and animal feedstuffs.

SUMMARY OF THE INVENTION

One embodiment of the invention relates to seed of a soybean cultivar designated S04-97130-15-02. The invention relates to the plant from the seed designated S04-97130-15-02, or the plant parts. The invention also encompasses a tissue culture of regenerable cells, cells or protoplasts being from a tissue selected from the group consisting of: leaves, pollen, embryos, meristematic cells, roots, root tips, anthers, flowers, ovule, seeds, stems, pods, petals and the cells thereof.

The invention in one aspect covers a soybean plant, or parts thereof, having all of the physiological and morphological characteristics of the soybean plant.

Another aspect of this invention is the soybean plant seed or derived progeny which contains a transgene which provides herbicide resistance, insect resistance, resistance to disease, resistance to nematodes, male sterility, or which alters the oil profiles, the fatty acid profiles, the amino acids profiles or other nutritional qualities of the seed.

The present invention further covers a method for producing a soybean seed with the steps of crossing at least two parent soybean plants and harvesting the hybrid soybean seed, wherein at least one parent soybean plant is the present invention. In another aspect of the invention covers the hybrid soybean seed and the progeny soybean plant and resultant seed, or parts thereof from the hybrid seed or plant or its progeny.

In an additional aspect, the invention covers a method for producing a soybean progeny from the invention by crossing soybean line S04-97130-15-02 with a second soybean plant to yield progeny soybean seed and then growing progeny soybean seed to develop a derived soybean line.

Yet another aspect of the invention covers a method for a breeding program using plant breeding techniques which employ the soybean plant S04-97130-15-02 as plant breeding material and performing breeding by selection techniques, backcrossing, pedigree breeding, marker enhanced selection, mutation and transformation.

DETAILED DESCRIPTION

The following data is used to describe and enable the present soybean invention.

| Soybean Data Collection | | | | |
|---|---|---|---|---|
| Core Traits | Abbr. | Description | Timing | Scale |
| Hila | HC | Phenotypic color; All experiments. | | G = Gray; BR = Brown; IB = Imperfect Black; Bl = Black; Y = Yellow; BF = Buff; IY = Imperfect Yellow; X = Mix |
| Flower | FC | Phenotypic color; All experiments. | | W = White; P = Purple; X = Mix |
| Pod | POD | Phenotypic color; All experiments. | | T = Tan; B = Brown; X = Mixed |
| Pubescence | PUB | Phenotypic color; All experiments. | | G = Gray; T = Tawny; LT = Light Tawny; X = Mixed |
| GWT | GWT | Grain weight/plot | Harvest | Pounds |
| H2O | H20 | Grain moisture/plot | Harvest | % moisture |
| Necessary Traits | Abbr. | | Timing | Scale |
| Hypocotyl Elongation | HYPO | Replicated Nursery | May to June | 1 to 5 (1 = best) |

-continued

| Soybean Data Collection | | | | |
|---|---|---|---|---|
| Seedling Establishment | EMG | 4 locations/test | VE-V1 | 1 to 5 (1 = best) |
| Maturity | MAT | 4 locations/test | | Taken in days after Aug. 31 |
| Plant Height | PLTHT | 4 locations/test | Harvest | Taken in inches |
| Branching | BR | 4 locations/test | R8-Harvest | 1 to 5 (1 = no branch) |

| Agronomic Traits | Abbr. | Opportunistic | Timing | Scale | |
|---|---|---|---|---|---|
| Green Lodging | GLOD | Where differential occurs. | R5 to R6 | 1 = All erect<br>2 = 67°<br>3 = 45°<br>4 = 22°<br>5 = 0° |  |
| Stem Lodging | LOD | Where differential occurs | Harvest | 1 = All erect<br>2 = 67°<br>3 = 45°<br>4 = 22°<br>5 = 0° |  |

| Core Traits | Abbr. | Description | Timing | Scale |
|---|---|---|---|---|
| Shatter | SHAT | Where differential occurs | Harvest | 1 to 5 (1 = best) |

| Opportunistic Disease Ratings | Abbr. | Key Maturities | Scale |
|---|---|---|---|
| Phytophthora Root Rot | PFT | All | 1 to 5 (1 = best) |
| Brown Stem Rot | BSR | G0 to EGIII | 1 to 5 (1 = best) |
| Sclerotinia White Mold | SWM | G0 to EGIII | 1 to 5 (1 = best) |
| Sudden Death Syndrome | SDS | EGII to GVII | 1 to 5 (1 = best) |
| Stem Canker | STMC | MGII to GVII | 1 to 5 (1 = best) |
| Charcoal Rot | CROT | LGIII to GVII | 1 to 5 (1 = best) |
| Frog Eye | FROG | EGIII to GVII | 1 to 5 (1 = best) |

| Disease Nurseries | Abbr. | Path | Timing | Scale |
|---|---|---|---|---|
| Iron Deficiency Chlorosis | IDC | Internal Field Nursery | June–July | 1 to 5 (1 = best) |
| Soybean Cyst Nematode | SCN | Race 3 Internal Nursery | Nov–April 30 d cycle | # = the race<br>R3 is resistant to race 3<br>MR14 is moderately resistant to race 14<br>R-MR-MS-S<br>R = resistant<br>S = susceptible<br>M = moderately |
| Phytophthora Root Rot PRR | PFT or PGR | | | 1 to 5 (1 = best) for field tolerance and resistance gene Rps 1a, Rps 1b, Rps 1c, Rps 1k, etc for specific genes. |
| Sudden Death Syndrome | SDS | | | Disease Severity Index or DSI. |
| Brown Stem Rot | BSR | | | 1 to 5 (1 = best) |
| Root Knot Nematode | RKN | | | R-MR-MS-S<br>R = resistant<br>S = susceptible<br>M = moderately |
| Stem Canker | STMC | | | 1 to 5 (1 = best) |

| Herbicide Evaluation | Abbr. | | | |
|---|---|---|---|---|
| Sulfentrazone | SULF | | | Sensitive, Tolerant |
| Metributzin | MET | | | Sensitive, Tolerant |

***All data to default to a "." (period) when data is not observed

TRAIT DEFINITIONS

Hypocotyl Elongation (HYPO) A rating of a variety's hypocotyl extension after germination when planted at a 5" depth in sand and maintained a warm germination environment for 10 days.

Seedling Establishment (EMG) A rating of the uniform establishment and growth of seedlings.

Maturity (MAT) The number of days after Aug. 31 when 95% of the main stem pods in the plot have reached their mature color.

Peroxidase Activity (Perox)—seed protein peroxidase activity is defined as a chemical taxonomic technique to separate cultivars based on the presence or absence of the peroxidase enzyme in the seed coat. Ratings are POS=positive for peroxidase enzyme or NEG=negative for peroxidase enzyme.

Plant Height (PLTHT) The average measured plant height in inches.

Branching (BRANCH) Rating of the number of branches and their relative importance to yield. This rating is taken at growth expressive locations.

Green Lodging (GLODGE) Rating based on the average of plants leaning from vertical in R5 to R6 stage.

Stem Lodging (LODGE) Rating based on the average of plants leaning from vertical at harvest.

Shatter (SHAT) Rating of pre-harvest loses based on amount of plants with open pods.

Iron Deficiency Chlorosis (IDC) A composite rating of Yellow Flash, Green-up, and Stunting in HpH soil. A 1 rating is the most positive for resistance to the symptoms listed and 5 is the least positive.

Phytophthora Root Rot (PGR) or (PFT) Greenhouse pot—root dip method for PFT and hypodermic needle method for rating PGR.

Root Knot Nematode (RKN) Greenhouse screen—30 day screen using infested soil. Rating Scale based upon female reproduction index on a susceptible check set where <10%=R; <30%=MR; <60%=MS; >60%=S.

Stem Canker (STC) Based on number of lesions, scale 1–5.

Sulfentrazone (SULF) Authority™ (commercial herbicide) Greenhouse nursery rating damage of multiple rates.

Metributzin (MET) Greenhouse nursery rating damage of multiple rates.

Definitions of Staging of Development

The plant development staging system employed in the testing of this invention divides stages as vegetative (V) and reproductive (R). This system accurately identifies the stages of any soybean plant. However, all plants in a given field will not be in the stage at the same time. Therefore, each specific V or R stage is defined as existing when 50% or more of the plants in the field are in or beyond that stage.

The first two stages of V are designated a VE (emergence) and VC (cotyledon stage). Subdivisions of the V stages are then designated numerically as V1, V2, V3 through V (n). The last V stage is designated as V (n), where (n) represents the number for the last node stage of the specific variety. The (n) will vary with variety and environment. The eight subdivisions of the reproductive stages (R) states are also designated numerically. R1=beginning bloom; R2=full bloom; R3=beginning pod; R4=full pod; R5=beginning seed; R6=full seed; R7=beginning maturity; R8=full maturity.

BROWN STEM ROT (BSR)—This disease is caused by the fungus *Phialophora gregata*. The disease is a late-season, cool-temperature, soilborne fungus which in appropriate favorable weather can cause up to 30 percent yield losses in soybean fields. For purposes of these tests the information is gathered in a greenhouse with a plant in a pot then a root dip procedure is employed.

SUDDEN DEATH SYNDROME (SDS)—This disease is caused by slow-growing strains of *Fursarium solani* that produce bluish pigments in culture. The disease is a mid to late season, soil borne disease that occurs in soybean fields with high yield potential. Yield losses may be total or severe in infected fields. Sudden Death Syndrome (SDS) is based on leaf area affected. The scale used for these tests is 1–5.

SOYBEAN CYST NEMATODE—The Soybean Cyst Nematode (SCN) *Heterodera glycines*, is a small plant-parasitic roundworm that attacks the roots of soybeans. Soybean Cyst Nematode (SCN) for purposes of these tests are done as a greenhouse screen—30 day screen using infested soil. The rating scale is based upon female reproduction index on a susceptible check set where <10%=R (RESISTANT); <30%=MR(MODERATELY RESISTANT); <60%=MS (MODERATELY SUSPECTIBLE); >60%=S (SUSPECTIBLE). In priority order, the screening races include: 3, 14, & 1.

MATURITY DATE. Plants are considered mature when 95% of the pods have reached their mature color. The number of days is either calculated from September 1 or from the planting date. (MR#) wherein # equals days.

RELATIVE MATURITY GROUP (RM). Industry Standard for varieties groups, based day length or latitude. Long day length (northern areas in the Northern Hemisphere) are classified as (Groups 000,00,0). Mid day lengths variety groups lie in the middle (Groups I–VI). Very short day lengths variety groups (southern areas in Northern Hemisphere) are classified as (Groups VII, VIII, IX).

SEED YIELD (Bushels/Acre). The yield in bushels/acre is the actual yield of the grain at harvest.

SHATTERING. The rate of pod dehiscence prior to harvest. Pod dehiscence involves beans dropping out of the pods. Shatter (SHAT) for these tests the rating of pre-harvest loses is based on amount of plants with open pods.

PLANT. Means the plant, the plant's cells, plant protoplasts, plant cells of tissue culture from which soybean plants can be regenerated, plant calli, plant clumps, and plant cells that are intact in plants or parts of the plants, such as pollen, nodes, roots, flowers, seeds, pods, leaves, stems, and the like.

The present invention is S04-97130-15-02. This soybean is developed for use of the beans. S04-97130-15-02 is a 2.0 relative maturity. S04-97130-15-02 is best suited to 15–30" row spacing; drilling is not as acceptable. This variety is an excellent choice in areas where there is Race 3 cyst nematode and better then average plant for use in pH soil. This line is a growthy plant type. This plant has good tolerance for sclerotina white mold. This cultivar's general area of adaptation in the U.S. includes most soil types found in South Dakota, Southern Minnesota. This line is carrying a glyphosate resistance gene from Monsanto.

The traits of the invention are listed below.

| Trait | |
|---|---|
| RM | 2 |
| HR-herbicide resistance | RR |

-continued

| Trait | |
|---|---|
| Flower Color | P |
| Pubescene Color | T |
| Pod Color | B |
| Hila Color | BR |
| Lust | DULL |
| Perox | POS |
| PFT | 3.0 |
| Hypo | 2.00 |
| IDC | 3.1 |
| PGR | Rps1c |

RR = glyphosate resistance
Rps1c means this plant has a specific gene for resistance to Phytophthora root rot The present has a specific gene for resistance to Phytophthora root rot, although the resistance rating is not particularly high.

The instant invention provides methods and composition relating to plants, seeds and derivatives of the soybean cultivar S04-97130-15-02. Soybean cultivar S04-97130-15-02 has superior characteristics. The S04-97130-15-02 line has been selfed sufficient number of generations to provide a stable and uniform plant variety.

Cultivar S04-97130-15-02 shows no variants other than expected due to environment or that normally would occur for almost any characteristic during the course of repeated sexual reproduction. Some of the criteria used to select in various generations include: seed yield, lodging resistance, emergence, appearance, disease tolerance, maturity, plant height, maturity and shattering data.

The inventor believes that S04-97130-15-02 is similar to the comparison varieties. However, as shown in the tables, S04-97130-15-02 differs from these cultivars.

Direct comparisons were made between S04-97130-15-02 and these competing commercial varieties. Traits measured included yield, maturity, moisture, branching, lodging, plant height, field emergence, protein and oil. The results of the comparison are presented in below. The number of tests in which the varieties were compared is shown. The deviation or difference of the results, T-value and the traits which showed a significant difference and the level of that significance are in the table.

The present invention S04-97130-15-02 can carry genetic engineered recombinant genetic material to give improved traits or qualities to the soybean. For example, but not limitation, the present invention can carry, the glyphosate resistance gene for herbicide resistance as taught in the Monsanto patents (WO92/00377, WO92/04449, U.S. Pat. No. 5,188,642 and U.S. Pat. No. 5,312,910) or STS mutation for herbicide resistance. Additional traits carried in transgenes or mutation can be transferred into the present invention. Some of these genes include genes that give disease resistance to sclerotina such as the oxalate oxidase (Ox Ox) gene as taught in PCT/FR92/00195 Rhone Polunc and/or an Ox Decarboxylate gene for disease resistance or genes designed to alter the soybean oil within the seed such as desaturase, thioesterase genes (shown in EP0472722, U.S. Pat. No. 5,344,771) or genes designed to alter the soybean's amino acid characteristics. This line can be crossed with another soybean line which carries a gene that acts to provide herbicide resistance or alter the saturated and/or unsaturated fatty acid content of the oil within the seed, or the amino acid profile of the seed.

The present invention S04-97130-15-02 is employed in a number of plot repetitions to establish trait characteristics.

| External Name | RM | HR | Hilum | PGR | BSR | IDC | SCN Race 3 | SCN Race 14 |
|---|---|---|---|---|---|---|---|---|
| S04-97130-15-02 | 2 | RR | BR | Rps1c | | 3.1 | R3 | R14 |
| 1812 RR/N | 1.8 | RR | IB | xRps1k6 | 1.9 | 2.7 | R3 | S14 |
| 2612 RR/N | 2.6 | RR | BL | | 2.3 | 2.9 | R3 | Mr14 |

HR = herbicide resistance

The traits of the present invention differ from the comparison commercial soybean lines in Hilum color and in PGR resistance gene and in resistance to Cyst nematode. All three lines are resistance to race 3. Only the present invention is also resistant to race 14.

The present invention S04-97130-15-02 is employed in a trialling for a number of characteristics. These tests allow the usefulness of the invention to be shown in light of the environmental genetic interactions.

| S04-97130-15-02 is carrying Glyphosate resistance gene. | | | | |
|---|---|---|---|---|
| Ent | Yld | Moist | Appearance | Branch |
| S04-97130-15-02 vs 1812RR/N | | | | |
| S04-97130-15-02 | 38.1 | 11.3 | 2.8 | 3.3 |
| 1812RR/N | 41.0 | 11.6 | 3.0 | 2.0 |
| # LOCS | 22.0 | 22.0 | 5.0 | 3.0 |
| Diff | −3.0 | −0.4 | −0.2 | 1.3 |
| Std | 6.5 | 0.7 | 0.4 | 0.6 |
| T-val | −2.2 | −2.4 | −1.0 | 4.0 |
| Prob | 0.043** | 0.024** | 0.4 | 0.057* |
| S04-97130-15-02 vs 2612RR/N | | | | |
| S04-97130-15-02 | 58.6 | 12.7 | 2.7 | 3.0 |
| 2612RR/N | 60.0 | 12.3 | 2.4 | 1.0 |
| # LOCS | 15.0 | 15.0 | 5.0 | 1.0 |
| Diff | −1.4 | 0.4 | 0.3 | 2.0 |
| Std | 5.4 | 0.5 | 1.5 | — |
| T-val | −1.0 | 3.0 | 0.5 | — |
| Prob | 0.3 | 0.009*** | 0.7 | — |

Moist = Moisture
Yld = Yield
*Significant at the 0.10 level
**Significant at the 0.05 level
***Significant at the 0.01 level

| Ent | BSR | Emergence | Lg | Mat |
|---|---|---|---|---|
| S04-97130-15-02 vs 1812RR/N | | | | |
| S04-97130-15-02 | 4.0 | 2.4 | 1.6 | 17.7 |
| 1812RR/N | 1.0 | 2.3 | 2.0 | 17.7 |
| # LOCS | 1.0 | 8.0 | 7.0 | 7.0 |
| Diff | 3.0 | 0.2 | −0.4 | 0.0 |
| Std | — | 0.3 | 0.7 | 1.0 |
| T-val | — | 2.1 | −1.6 | 0.0 |
| Prob | — | 0.080* | 0.2 | 1.0 |
| S04-97130-15-02 vs 2612RR/N | | | | |
| S04-97130-15-02 | 2.0 | 3.0 | 1.6 | 17.0 |
| 2612RR/N | 2.0 | 3.0 | 1.4 | 21.8 |
| # LOCS | 1.0 | 2.0 | 10.0 | 6.0 |
| Diff | 0.0 | 0.0 | 0.3 | −4.8 |
| Std | — | 0.0 | 0.5 | 2.2 |

-continued

S04-97130-15-02 is carrying Glyphosate resistance gene.

| | | | | |
|---|---|---|---|---|
| T-val | — | — | 1.5 | −5.5 |
| Prob | — | — | 0.2 | 0.003*** |

Lg = lodging
Mat = maturity in days after September 1

| Ent | Pltht | PRR | Shatter | IDC |
|---|---|---|---|---|
| S04-97130-15-02 vs 1812RR/N | | | | |
| S04-97130-15-02 | 33.3 | — | — | 3.1 |
| 1812RR/N | 38.8 | — | — | 2.7 |
| # LOCS | 6.0 | 0.0 | 0.0 | 3.0 |
| Diff | −5.5 | — | — | 0.4 |
| Std | 3.3 | — | — | 0.7 |
| T-val | −4.1 | — | — | 0.9 |
| Prob | 0.010*** | — | — | 0.5 |
| S04-97130-15-02 vs 2612RR/N | | | | |
| S04-97130-15-02 | 33.6 | — | — | 3.1 |
| 2612RR/N | 32.0 | — | — | 3.5 |
| # LOCS | 5.0 | 0.0 | 0.0 | 4.0 |
| Diff | 1.6 | — | — | −0.3 |
| Std | 4.1 | — | — | 0.6 |
| T-val | 0.9 | — | — | −1.1 |
| Prob | 0.4 | — | — | 0.4 |

Pltht = plant height

The present invention is providing yield that is significantly less than one of the comparison commercial lines and which compares to the other. Each of these lines has their own positive traits. Each of these lines is different from the present invention. The present invention has significantly less moisture than does the line that showed more yield. The present invention is not showing Emergence of the present invention is significantly different for one line but is similar for the other line. The yield and other data is a snapshot of each of these lines' results in the specific environment and will differ when other environmental interactions are measured.

This S04-97130-15-02 invention was compared with a commercial soybean product for certain grain quality traits. The tests were run in 3 locations. The data in the first set shows that seed sizes are very similar for the present invention when compared to the other lines. The protein in this test data do not differ significantly. In one instance the present invention has no significant difference in oil percentage, in the other comparison there is a significant difference.

Test Data 1

| Ent | % Oil | % Protein | sds per lb |
|---|---|---|---|
| S04-97130-15-02 vs 1812RR/N | | | |
| S04-97130-15-02 | 20.7 | 42.2 | 2400–3200 |
| 1812RR/N | 20.6 | 41.9 | 2300–3300 |
| # LOCS | 3.0 | 3.0 | |
| Diff | 0.1 | 0.3 | |
| Std | 0.7 | 1.2 | |
| T-val | 0.2 | 0.4 | |
| Prob | 0.9 | 0.7 | |
| S04-97130-15-02 vs 2612RR/N | | | |
| S04-97130-15-02 | 20.1 | 41.6 | 2400–3200 |
| 2612RR/N | 20.7 | 41.6 | 2300–3300 |
| # LOCS | 3.0 | 3.0 | |
| Diff | −0.6 | 0.1 | |
| Std | 0.3 | 1.6 | |
| T-val | −3.7 | 0.1 | |
| Prob | 0.1* | 1.0 | | sds per lb = seeds per pound

This invention also is directed to methods for producing a new soybean plant by crossing a first parent plant with a second parent plant wherein the first or second parent plant is the present invention. Additionally, the present invention maybe used in the variety development process to derive progeny in a breeding population or crossing. Further, both first and second parent plants can come from the soybean line S04-97130-15-02. A variety of breeding methods can be selected depending on the mode of reproduction, the trait, the condition of the germplasm. Thus, any such methods using the S04-97130-15-02 are part of this invention: selfing, backcrosses, recurrent selection, mass selection and the like. The scope of the present invention includes any use on S04-96289-A99-31240 of marker methods. Through the use of markers such as SSRs, RFLP's, Snps, Ests, AFLPs, gene primers, and the like to identify genetic alleles which can be identified and breed with marker assistance into the present invention with little to no superfluous germplasm being dragged into the present invention. This results in formation of the present invention plus for example, cyst nematode resistance, brown stem rot resistance, phytothora resistance, IDC resistance and the like. This is often referred to as targeted trait introduction. The result being the present invention plus the genetic allele carrying the specific desired trait from other soybean germplasm.

The scope of the present invention includes any use on S04-97130-15-02 of transformation methods. Transformation methods are means for integrating new genetic coding sequences (transgenes) into the plant's genome by the incorporation of these sequences into a plant through man's assistance. Many dicots including soybeans can easily be transformed with Agrobacterium. The most common method of transformation after the use of agrobacterium is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art. The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

After the transformation of the plant material is complete, the next step is identifying the cells or material, which has been transformed. In some cases, a screenable marker is employed such as the beta-glucuronidase gene of the uidA locus of E. coli. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular are well known in the art. The plants from the transformation process or the plants resulting from a cross using a transformed line or the progeny of such plants are transgenic plants that carry the transgene.

DEPOSIT INFORMATION

A seed deposit of the Garst Seed Company's soybean cultivar S04-97130-15-02 disclosed above and recited in the appended claims will be made with the American Type Culture Collection (ATCC), 10801 University Boulevard, Manassas, Va. 20110. The date of deposit was Nov. 8, 2006. The deposit of 2,500 seeds maintained by Garst Seed Company since prior to the filing date of this application. All restrictions on the deposit upon issuance of the patent will be removed, and the deposit is intended to meet all of the requirements of 37 C.F.R. §§ 1.801–1.809. The ATCC accession number is PTA-7991. The viablity of the deposit was positive in tests ran on Nov. 20, 2006. The deposit will be maintained in the depository for a period of 30 years, or 5 years after the last request, or for the effective life of the patent, whichever is longer, and will be replaced as necessary during that period.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

What is claimed is:

1. A soybean seed designated S04-97130-15-02, a sample of said seed deposited under ATCC Accession No. PTA-7991.

2. A plant, or parts thereof, produced by growing the seed of claim 1.

3. Pollen of the plant of claim 2.

4. A soybean plant, or parts thereof, having all of the physiological and morphological characteristics of the soybean plant of claim 2.

5. A tissue culture of regenerable cells of the soybean plant of claim 2.

6. The tissue culture according to claim 5, wherein the cells are obtained from the group consisting of leaves, pollen, embryos, meristematic cells, roots, root tips, anthers, stomatal cells, flowers, seeds, stems and pods.

7. A soybean plant regenerated from the tissue culture of claim 6, having all of the morphological and physiological characteristics of soybean cultivar S04-97130-15-02.

8. A method for producing a soybean seed comprising crossing two soybean plants and harvesting the resultant soybean seed, wherein at least one soybean plant is the soybean plant of claim 2.

9. A method for producing a hybrid soybean seed comprising crossing the soybean plant according to claim 2 with a second soybean plant and harvesting the resultant hybrid soybean seed.

10. A method for producing a S04-97130-15-02-derived soybean plant, comprising:
    a) crossing soybean line S04-97130-15-02, a sample of said line deposited under ATCC Accession No. PTA-7991, with a second soybean plant to yield progeny soybean seed; and
    b) growing said progeny soybean seed to yield said S04-97130-15-02-derived soybean plant.

11. The method of claim 8, wherein the second soybean plant is transgenic.

12. The method of claim 11 wherein the transgenic soybean plant contains genetic material conferring a trait selected from the group consisting of herbicide resistance, insect resistance, resistance to disease, and male sterility.

13. The method of claim 12 wherein the resistance to disease is through an oxalate oxidase encoding polynucleotide sequence or an oxalate decarboxylate encoding polynucleotide sequence.

* * * * *